United States Patent [19]

Takahashi et al.

[11] Patent Number: 5,349,940
[45] Date of Patent: Sep. 27, 1994

[54] ENDOSCOPE SYSTEM WITH A ROTATING TREATMENT ADAPTER AT THE END

[75] Inventors: Ichiro Takahashi, Hachioji; Yasundo Tanaka, Urawa; Katsunori Sakiyama, Akigawa, all of Japan

[73] Assignee: Olympus Optical Co., Ltd., Tokyo, Japan

[21] Appl. No.: 818,128

[22] Filed: Jan. 8, 1992

[30] Foreign Application Priority Data

Jan. 10, 1991 [JP] Japan .................. 3-001472
Mar. 19, 1991 [JP] Japan .................. 3-054873
Nov. 22, 1991 [JP] Japan .................. 3-308028

[51] Int. Cl.$^5$ .......................................... A61B 1/00
[52] U.S. Cl. .......................... 128/4; 356/241; 403/349
[58] Field of Search ............ 279/23.1, 24, 19.5, 279/906, 9.1; 408/226; 128/4, 6, 7; 403/19, 20, 315, 316, 348, 349, 320; 356/241

[56] References Cited

U.S. PATENT DOCUMENTS

| | | | |
|---|---|---|---|
| 4,076,105 | 2/1978 | Aono | 403/349 X |
| 4,186,762 | 2/1980 | Hardin | 403/349 X |
| 4,203,444 | 5/1980 | Bonnell et al. | |
| 4,237,091 | 12/1980 | Lobdell et al. | 403/349 X |
| 4,661,009 | 4/1987 | Tripp | 403/349 |
| 4,943,182 | 7/1990 | Hoblingre | 403/349 |
| 5,018,901 | 5/1991 | Ferree et al. | 403/316 X |
| 5,123,904 | 6/1992 | Shimomura et al. | 604/22 |

FOREIGN PATENT DOCUMENTS 58-83949  5/1983  Japan .
58-162924 9/1983  Japan .

Primary Examiner—Richard J. Apley
Assistant Examiner—Karen A. Jalbert
Attorney, Agent, or Firm—Armstrong, Westerman, Hattori, McLeland & Naughton

[57] ABSTRACT

The distal end of an endoscope is provided with at least an objective optical system and a torque transmission member for supporting a rotating treatment member. The distal end of the torque transmission member comprises a hollow to which a support axis formed in the rotating treatment member is fitted, a slit for guiding a protrusion formed on the external circumference of the support axis, and a locking member for locking the protrusion in the slit. Torque is transmitted from the torque transmission member to the rotating treatment member by means of the protrusion formed on the external circumference of the support axis of the rotating treatment member and the slit formed on the torque transmission member for guiding the protrusion.

25 Claims, 16 Drawing Sheets

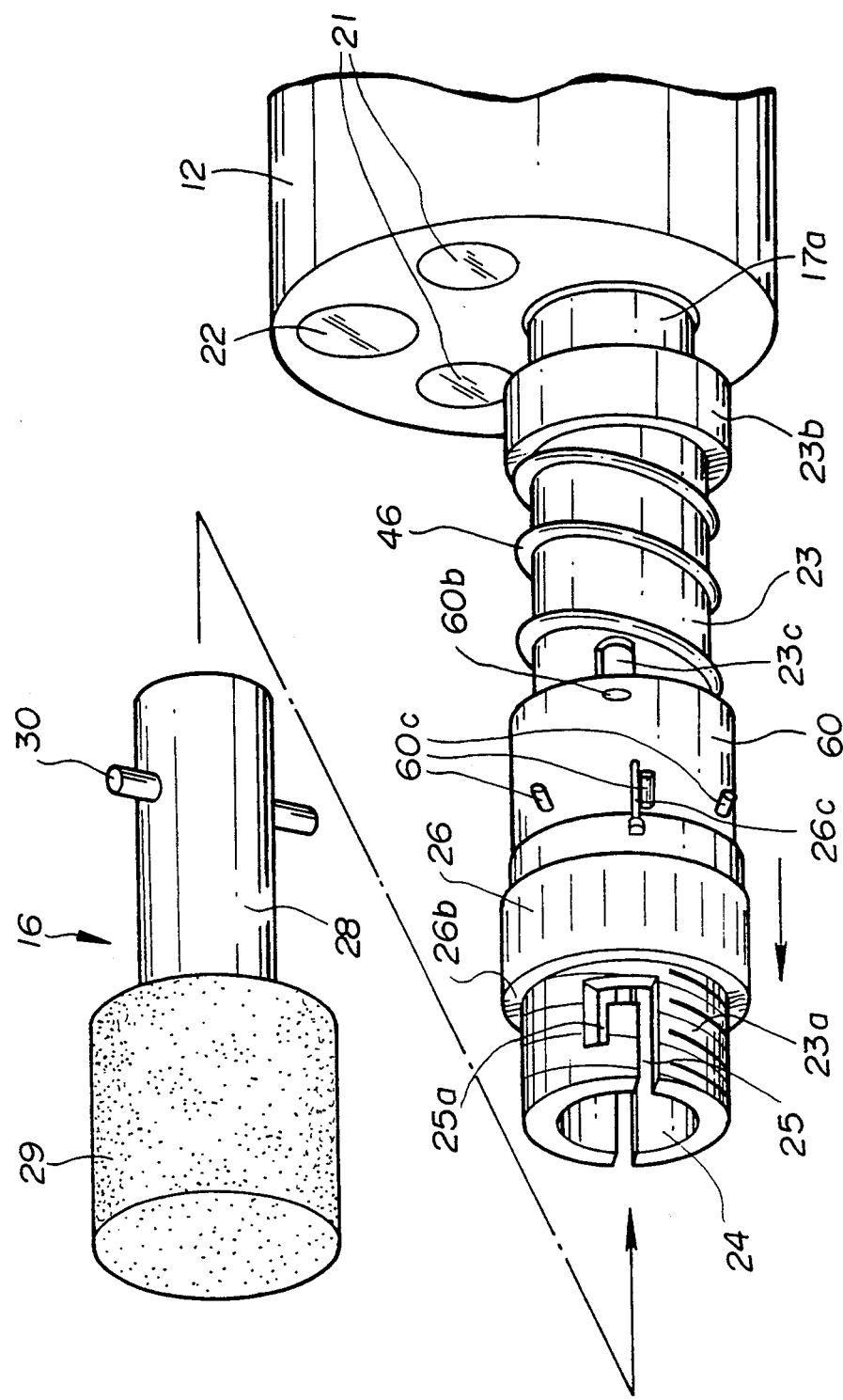

ENDOSCOPE SYSTEM WITH A ROTATING TREATMENT ADAPTER AT THE END

BACKGROUND OF THE INVENTION

1. Field of the Invention

The present invention relates to an endoscope system with a rotating treatment adapter at the end. More particularly, this invention is concerned with an endoscope system having a mounting mechanism for preventing the falling of a rotating treatment member to be mounted at the end of a torque coupling member.

2. Description of the Prior Art

In recent years, an industrial endoscope allowing a worker to check the inside of a pipe or an engine at a chemical plant without disassembling it has been adopted widely.

For example, an endoscope is used to check a jet engine. Then, a defect or other damage may be detected on the edge of a turbine blade which is driven to rotate. In this case, even a minor damage causes concentration of stress, supposing it is left intact. As a result, the damage grows to necessitate replacement of the blade unit.

Therefore, in the past, even when replacement is not needed, if a damage is detected, the engine has been disassembled to grind the cracked part and its surrounding area. This procedure is, however, time-consuming.

In an endoscope of prior art disclosed, for example, in Japanese Patent Laid-Open No.58-162924, a grindstone or other rotating treatment member is mounted to the distal end of the endoscope. Then, the rotating treatment member is inserted into a jet engine to grind a damaged part.

This kind of rotating treatment member is often mounted to the end of an insertion tube of an endoscope to be detachable from a torque transmission member for transmitting torque via a tightening means including a screw, a three-claw chuck, and a collet chuck. Thus, the rotating treatment member can be changed depending on the purpose of treatment or use.

For example, when the blade of a jet engine is treated using an endoscope having a rotating treatment member, a grindstone must be assuredly prevented from falling into the engine.

In general, when a metal plate is ground, the ground portion of the metal plate is misshaped depending on the rotating direction of a grindstone. Therefore, the rotating direction of a grindstone must be changed selectively. Assuming that a grindstone is attached or detached using a screw, when the grindstone is pressed to a blade for treatment, if it is rotated in the direction of loosening the engagement with a torque transmission member, it will fall off. Therefore, the rotating direction is confined to one direction and cannot be changed selectively.

A three-claw chuck or a collet chuck uses frictional force alone to fix a grindstone to a torque transmission member. Therefore, if the chuck is loosened even slightly, it may cause the grindstone to fall off. The use of an endoscope having a rotating treatment member fixed with a three-claw or collet chuck must be allowed only under the conditions that the relationship between tightening force and transmission torque is well-understood and it is confirmed that the grindstone will not fall off. Thus, when an endoscope having a rotating treatment member fixed with a three-claw or collet chuck is employed, it must be checked whether the use of the endoscope is limited or not. This deteriorates workability.

SUMMARY OF THE INVENTION

The principal object of the present invention is to provide an endoscope system in which a rotating treatment member can be mounted to the end of a torque transmission member easily and securely without being dropped so that it can be rotated or reversed.

Another object of the invention is to provide an endoscope system which can vary the grinding characteristic depending on the purpose of use and thus permits flexible treatment.

The other object of the invention is to provide an endoscope system to which a rotating treatment member can be mounted easily and securely regardless of its rotating direction so that it will not fall off.

In an endoscope system according to the present invention, the distal end of an endoscope is provided with at least an objective optical system and a torque transmission member for supporting a rotating treatment member. The distal end of the rotating transmission section is provided with a hollow into which a support axis of the rotating treatment member is fitted, a slit for guiding a protrusion formed on the external circumference of the support axis, and a locking member for locking the protrusion in the slit. Torque is transmitted from the torque transmission member to the rotating treatment member by means of the protrusion on the external circumference of the support axis of the rotating treatment member and the slit formed on the torque transmission member for guiding the protrusion. The protrusion is locked in the slit using the locking member. Therefore, when the rotating treatment member is rotated clockwise or counterclockwise, the coupling between the torque transmission member and rotating treatment member will not be released. This successfully prevents the rotating treatment member from falling off.

BRIEF DESCRIPTION OF THE DRAWINGS

FIG. 1 is a perspective view of the distal end of an endoscope;

FIG. 2 is a side view showing a torque transmission member and a rotating treatment member;

FIG. 3 is a side view showing the torque transmission member and rotating treatment member which are tightened mutually;

FIG. 4 is a perspective view of a locking member;

FIG. 5 is an overall configuration drawing of the endoscope system;

FIG. 6 shows the A—A cross section of FIG. 1 showing the configuration of the tip of the endoscope;

FIG. 7 is a cross-sectional drawing showing the configuration of the back of the endoscope;

FIG. 8 is an explanatory drawing showing that the ground portion is misshaped depending on the rotating direction;

FIG. 9 is an overall configuration drawing of a modified endoscope system of the first embodiment;

FIG. 10 is a side view of a torque transmission member and a rotating treatment member which are tightened mutually;

FIG. 11 shows the B—B cross section of FIG. 10;

FIG. 12 is a perspective drawing of a rotating treatment member;

FIG. 13 is a front view of a locking member;

FIG. 14 is a perspective drawing of a rotating treatment member;

FIG. 15 is a front view of a locking member;

FIG. 16 is a side view of a torque transmission member and a rotating treatment member mounted to the torque transmission member;

FIG. 17 is an exploded view of the torque transmission member and rotating treatment member;

FIG. 18 is a perspective drawing of the distal end of an endoscope;

FIG. 19 is a side view of a rotating treatment member and a torque transmission member to which the rotating treatment member is mounted;

FIG. 21 is a perspective view showing the distal end of an endoscope according to the seventh embodiment of the present invention;

FIG. 23 is a schematic drawing of an endoscope system;

FIG. 24 is a perspective drawing of a rotating treatment member and the distal end of the endoscope;

FIG. 25 is a cross-sectional drawing of the distal end of the endoscope to which the rotating treatment member is mounted;

FIG. 26 is a cross-sectional drawing of the rotating treatment member and the flexible shaft unit;

FIG. 27 shows the joint of the motor of an endoscope control section and the flexible shaft; and FIG. 28 is a perspective drawing showing the joint member of the motor and flexible shaft.

DETAILED DESCRIPTION OF THE PREFERRED EMBODIMENTS

Embodiments of the present invention are explained in conjunction with the drawings below.

Figure 5:
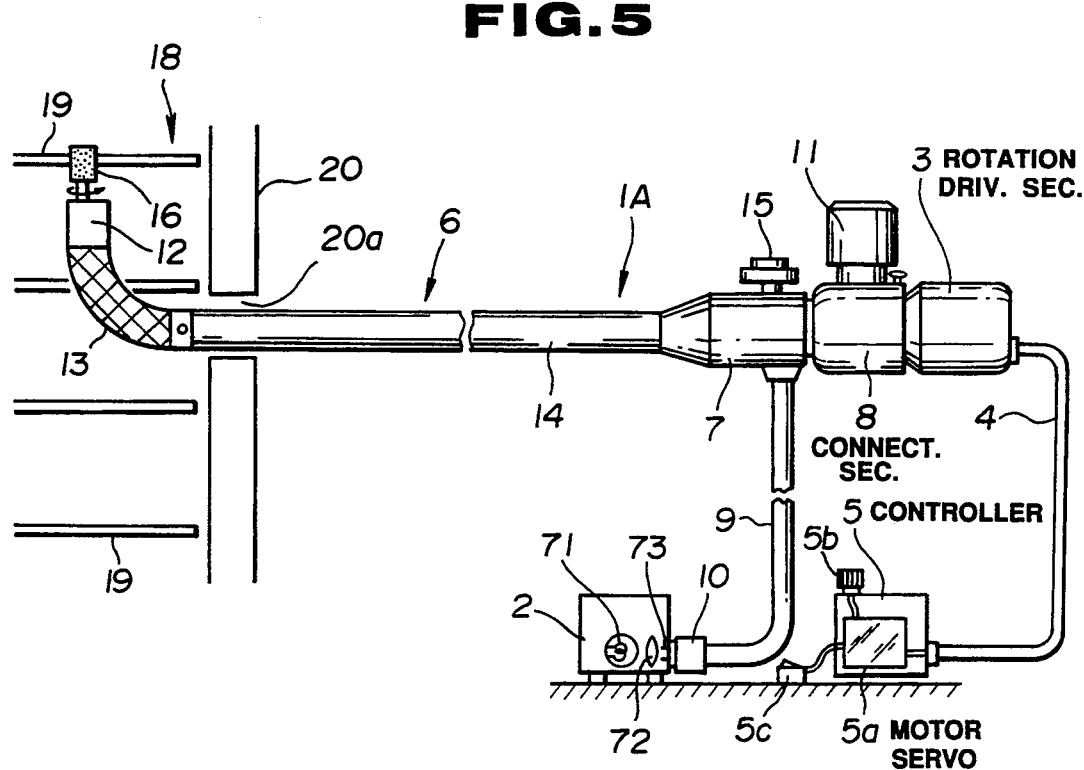

As shown in FIG. 5, an endoscope system according to the first embodiment comprises an endoscope 1A, a light source 2 which is connected to the endoscope 1A via a light guide cord 9 and supplies illumination light, a rotation drive 3 which is connected to a connecting section 8 of the endoscope 1A and generates rotation driving force, and a controller 5 which is connected to the rotation drive 3 via cord 4 and controls the rotation of the rotation drive 3.

The endoscope 1A comprises an elongated insertion tube 6, a control section 7 coupled to the back of the insertion tube 6, a connecting section 8 which is coupled to the back or the control section 7 and transmits torque from the rotation drive 3 to the proximal end of a torque transmission member, and a light guide cord 9 extending outward from the side of the control section 7.

The end of the light guide cord 9 is freely detachable from the light source 2 using a connector 10. When the light source 2 is connected with the connector 10, the light of a lamp 71 inside the light source 2 is converged on a condenser lens 72 to supply illumination light onto the end surface of a light guide 73 running through the light guide cord 9. The light guide 73 propagates the illumination light supplied onto the end surface and emits it from the other end surface fixed to the distal end 12 of the insertion tube 6. The light is emitted via an illumination optical system 21 to illuminate a subject in the advancing direction.

The insertion tube 6 is divided into a rigid distal end 12, a bending section 13 which can bend, and a rigid section 14 in that order from the tip of the endoscope. An angulation knob 15 for bending the bending section 13 is installed in the side of the control section 7.

Figure 1:
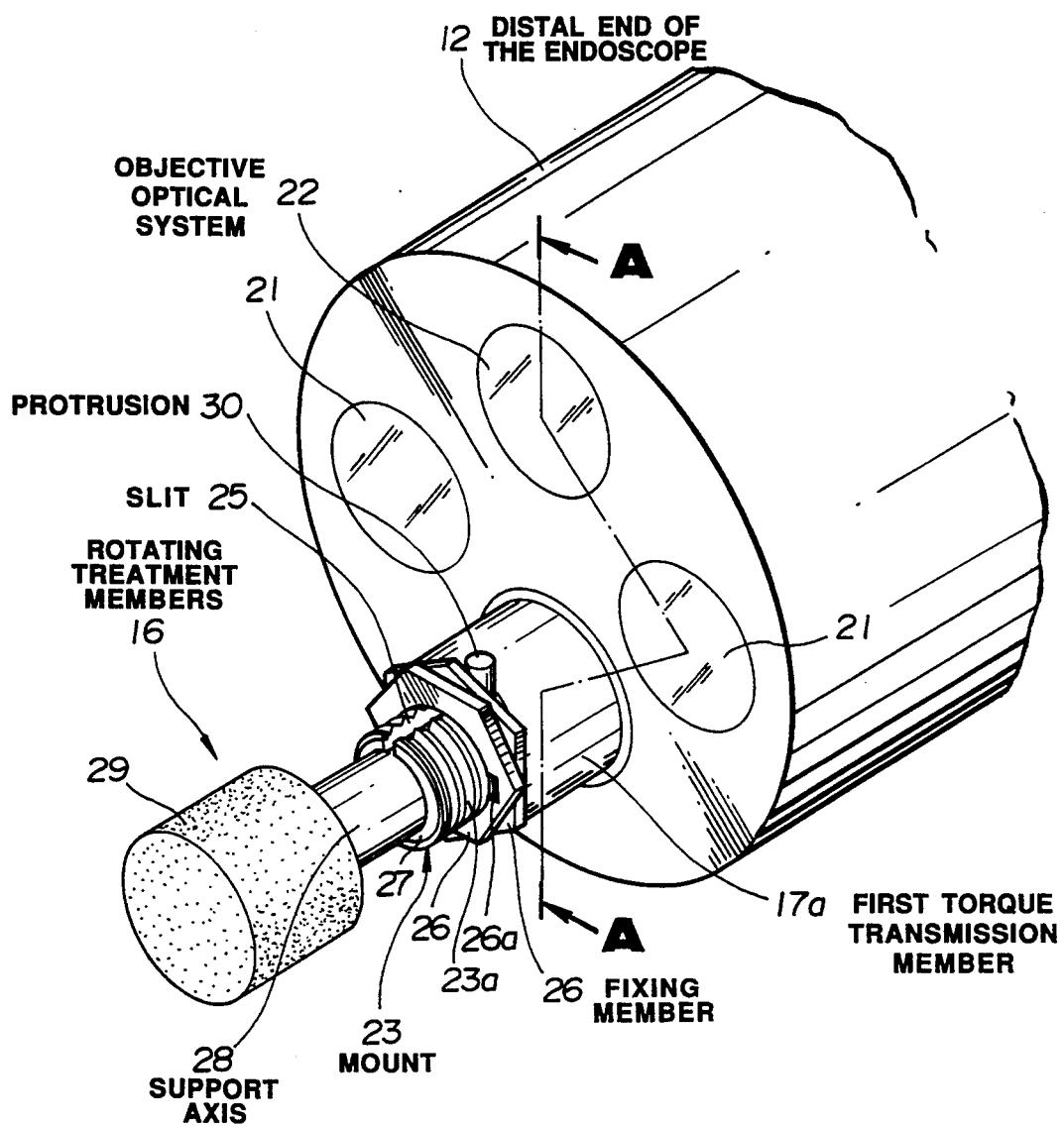
FIGS. 1 to 9 relate to the first embodiment of the present invention.
Figure 6:
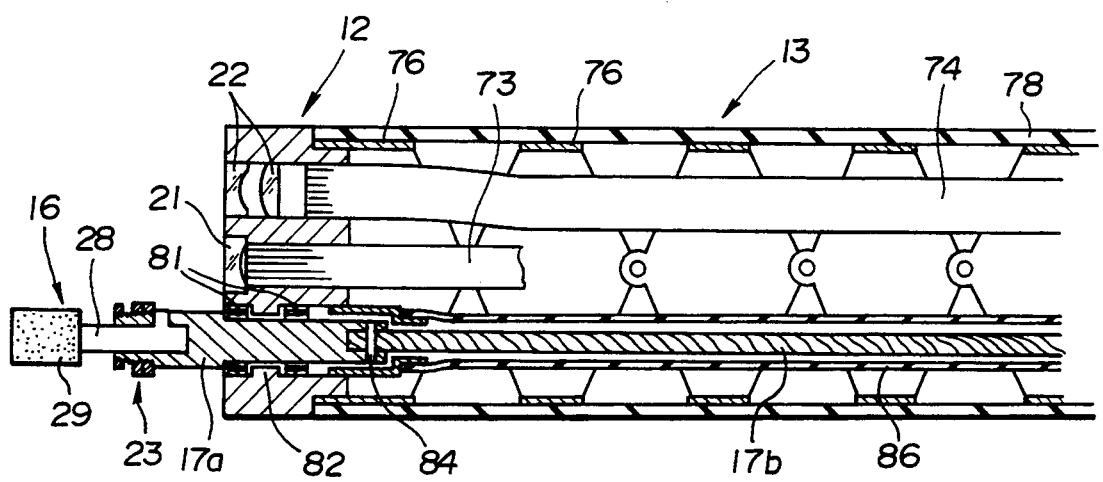
Figure 7:
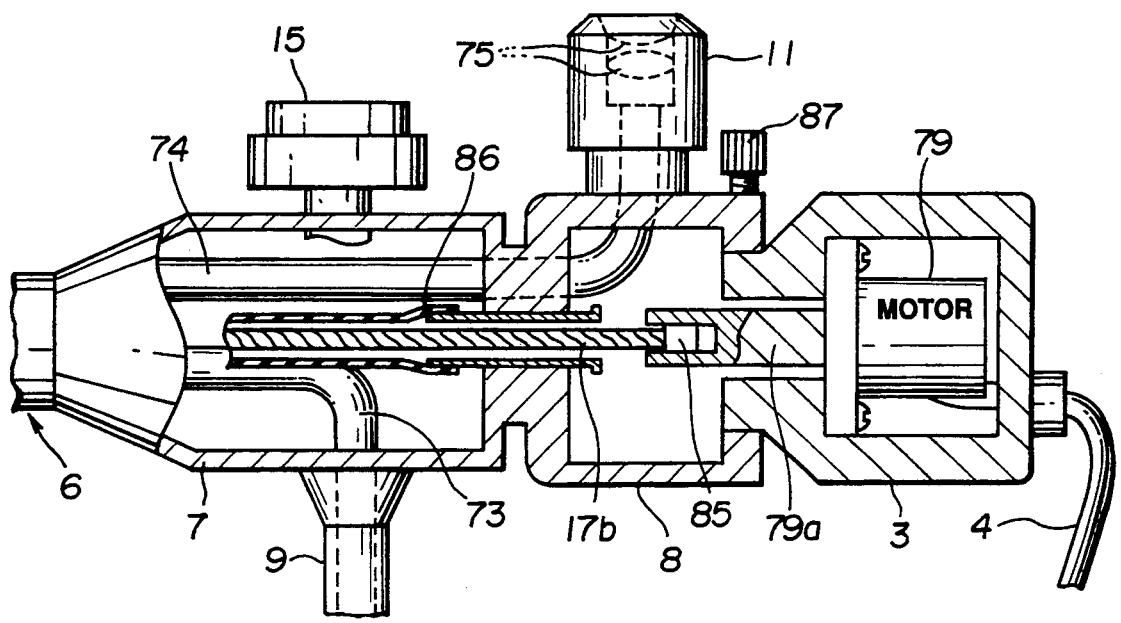

As shown in FIGS. 1 and 6, the distal end 12 of the insertion tube 6 is provided with an objective optical system 22 for forming images of subjects which adjoins the illumination optical system 21 for emitting illumination light. As shown in FIG. 6, the end surface of an image guide 74 having a function for transferring optical images is fixed to the distal end 12 as a focal surface of the objective optical system 22. An image formed on the end surface is transferred to the other end surface fixed to an eyepiece unit 11 on the side of the connecting section 8 as shown in FIG. 7. Then, the optical image is transferred by an eyepiece 75 on the opposite side of the other end surface. Finally, the enlarged image can be observed with naked eyes.

On the external circumference of the back of the distal end 12, distal joint chips 76 are fixed to form the bending section 13. Each joint chip 76 is coupled to adjacent joint chips 76 with a rivet so that it can rotate freely. That is to say, two joint chips 76 located side by side in the longitudinal direction of the insertion tube 6 are coupled mutually to be rotatable freely, thus forming the bending section 6. The tip of wire which is not illustrated is fixed to the distal joint chips 76, and the back of the wire, to a pulley, which is not illustrated, on the axis of the angulation knob 15. When the angulation knob 15 is rotated, one of a wire pair is hauled in, and the other is loosened so that it can bend toward the hauled wire. Joint chips 76 forming the bending section 6 are covered with a flexible tube 78.

As shown in FIGS. 1 to 6, the tip of a first torque transmission member 17a forming a torque transmission means is mounted to the distal end 12 so that the first torque transmission member 17a can rotate freely. The tip of the first torque transmission member 17a coming out of the end surface of the distal end 12 is provided with a mount 23. To the mount 23, the rotating treatment member 16 can be mounted to be freely detachable. As shown in FIG. 6, the tip of a second torque transmission member 17b is mounted to the back (proximal end) of the first torque transmission member 17a. As shown in FIG. 7, the back of the second torque transmission member 17b is to be coupled to a rotation axis 79a of a motor 79 forming the rotation drive 3 in the connecting section 8.

More specifically, the rotating treatment member 16 is coupled to the motor 79 of the rotation drive 3 via the torque transmission members 17a and 17b, that is; the torque of the motor 79 is transmitted to the rotating treatment member 16 via the torque transmission members 17a and 17b, thus driving the rotating treatment member 16 to rotate.

As shown in FIG. 6, the proximal side of the first torque transmission member 17a is made smaller in diameter. The small-diameter portion is held by the distal end 12 using bearings 81 which are engaged with recesses on the distal end 12, so that it can be rotated freely. A protrusion 82 is formed to match the hole interposing between the bearings 81 to restrict the axial movement of the first torque transmission member 17a, so that the first torque transmission member 17a will not fall off.

The tip of the second torque transmission member 17b is fitted into the hole at the proximal end of the first torque transmission member 17a. Moreover, a pin 84 is fitted into the hole laterally and secured, for example, with adhesive. The second torque transmission member 17b is formed, for example, with twisted wires to ensure higher flexibility than it is formed with a single wire. The back of the second torque transmission member 17b is, as shown in FIG. 7, fitted into the hole of the rotation axis 79a of the motor 79 in the connecting section 8. This hole is, for example, a square, to which a square member 85 formed on the back of the second torque transmission member 17b is fitted. Then, in whichever direction the motor 79 is rotated, the rotation can be transmitted to the second torque transmission member 17b.

The second torque transmission member 17b is running through the flexible tube 86. The tip and back of the tube 86 are locked with metallic rings. The rotation drive 3 is, as shown in FIG. 7, fitted into the opening in the back of the connecting section 8 and secured with a screw 87 to be freely detachable.

In FIG. 5, 18 denotes a jet engine as a subject. An access port 20a is drilled through a partition 20 shielding compressor blades 19 of the jet engine 18, through which the distal end 12 of the insertion tube 6 of the endoscope 1 is inserted inward.

Figure 2:
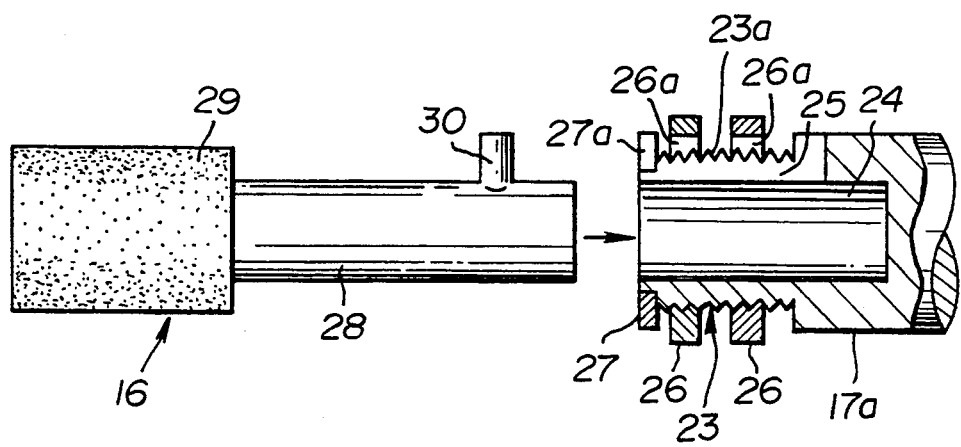
Figure 3:
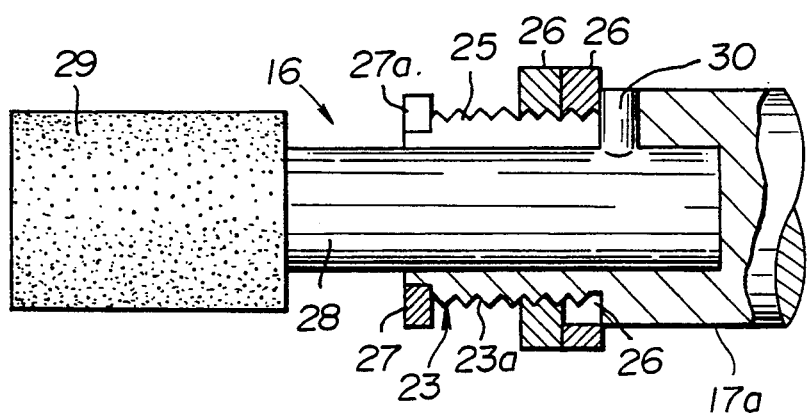
Figure 4:
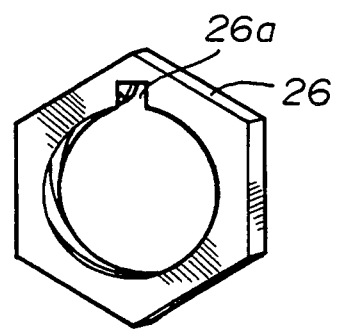

As shown in FIGS. 2 and 3, a hollow 24 is created in the rotation center of the mount 23 of the first torque transmission member 17a. A screw thread 23a is created on the external circumference of the mount 23. A slit is formed from the edge in the axial direction.

Two locking members (nut) 26 are applied to the screw thread 23a. A clearance groove 26a having the same width as that of the slit 25 is formed in the internal-diameter side of each of the locking members 26. A stopper 27 is adhered to the edge of the screw thread 23a using, for example, adhesive. A clearance groove 27a is created in the area of the stopper 27 that coincides with the slit 25.

At the tip of a support axis 28 of the rotating treatment member 16, a grindstone 29 is installed to grind or polish a subject it touches on its side when rotated. A protrusion 30 is created on the external circumference of the support axis 28.

The proximal portion of the support axis 28 of the rotating treatment member 17 is fitted into the hollow 24 of the mount 23 for the first torque transmission member 17a so that it can be rotated freely. The protrusion 30 is engaged with the slit 25 formed on the mount 23 to move freely.

As shown in FIG. 5, a controller 5 incorporates a motor servo circuit 5a for stabilizing the rotation speed of the motor 79, and is provided with a rotation speed adjustment knob for varying the rotation speed to be stabilized. A foot switch 5c for rotating or reversing the motor 79 is extending from the controller 5.

Next, the functions of the first embodiment having the foregoing configuration are explained.

When a rotating treatment member 16 is mounted to a first torque transmission member 17a protruding from the end surface of the distal end 12 of an endoscope 1A, the clearance grooves 26a of two locking members 26 applied to the screw thread 23a of a mount 23 are aligned with a slit 25 formed on the mount 23 (FIG. 2).

Next, the back of a support axis 28 of the rotating treatment member 16 is inserted into a hollow 24 created in the distal end 12. At the same time, a protrusion 30 formed on the external circumference of the support axis 28 is inserted into the slit 25.

Then, after the support axis 28 is fitted into the hollow 24 properly, the locking members 26 are rotated to tighten the protrusion 30 protruding from the support axis 28.

When the locking members 26 are tightened, the clearance grooves 26a of the locking members 26 are mismatched with the protrusion 30. This locks the protrusion 30. Then, the rotating treatment member 16 is fixed to the first torque transmission member 17a. When the two locking members 26 are rotated to tighten the protrusion 30, they serve as lock nuts. This ensures more reliable fixation.

After that, when a grindstone 29 or the rotating treatment member 16 fixed properly to the first torque transmission member 17a installed at the distal end 12 of the endoscope 1A is used to repair the damaged portion of, for example, a compressor blade 19 of a jet engine 18, an operator inserts the distal end 12 of the endoscope 1A into an access port 20a drilled through a partition 20 of the jet engine 18, feeds an insertion tube 6 consecutively while observing the image formed in an eyepiece unit 11, then detects the damaged portion of the compressor blade 19.

Then, when the damaged portion of the compressor blade 19 is detected, a controller 5 is operated to rotate the torque transmission member 17a via a rotation drive 3. Then, torque is transmitted to the rotating treatment member 16 via the protrusion 30 locked in the slit 25 on the mount 23 of the torque transmission member 17a. Finally, the rotating treatment member 16 rotates at a high speed.

Then, the grindstone 29 rotating at a high speed is pressed onto the damaged portion of the compressor blade 19 to grind it for treatment.

Figure 8:
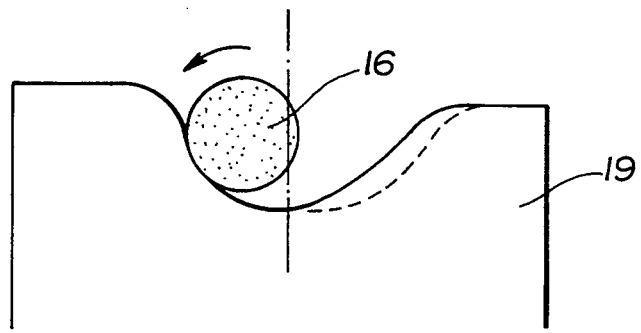

By the way, when the grindstone 29 is used for grinding, the ground portion is misshaped depending on the rotating direction as shown in FIG. 8. Therefore, if treatment is initiated by clockwise rotation, it should be followed by counterclockwise rotation. Thus, consideration must be taken into the rotating direction of a grindstone so that no portion will be misshaped. If necessary, a knob 5b can be used to specify the rotation speed suitable for a treatment.

Torque is transmitted to the grindstone 29 by the engagement between the slit 25 and protrusion 30. Therefore, the torque will not be transmitted to the locking members 26. This means that whichever direction the grindstone 29 is rotated; clockwise or counterclockwise, the locking members 26 will not be loosened and the rotating treatment member 16 will not come off from the torque transmission member 17a.

If the locking members 26 should be loosened by the influence of vibration, unless the clearance grooves 26a of the two locking members 27 coincide with the slit 25, the rotating treatment member will not fall off. The falling possibility is extremely low. Therefore, if three or more locking members 26 are applied, the falling possibility is further lowered.

Figure 9:
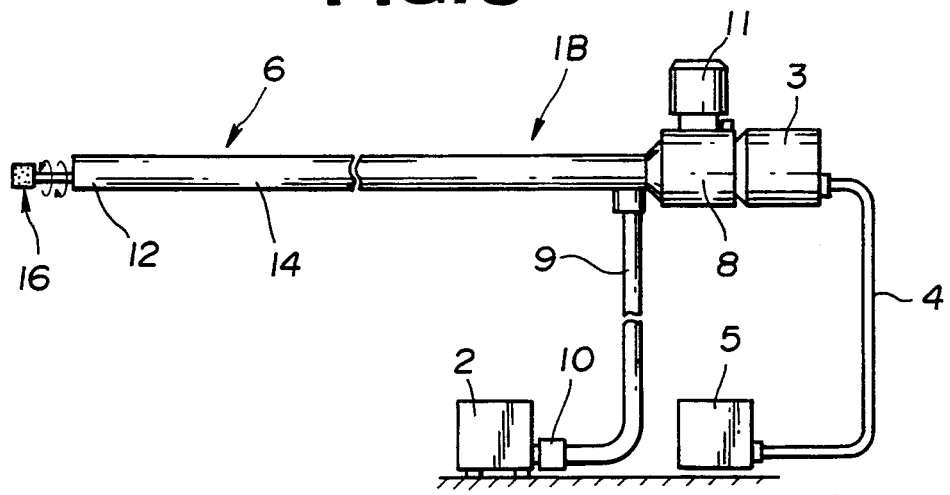

FIG. 9 shows an endoscope 1B in which an insertion tube 6 is formed only with a rigid section 14. The present invention can apply to either the endoscope 1A or 1B. In addition, the insertion tube 6 may be an interlock-type spiral tube or a semi-rigid tube.

Figure 10:
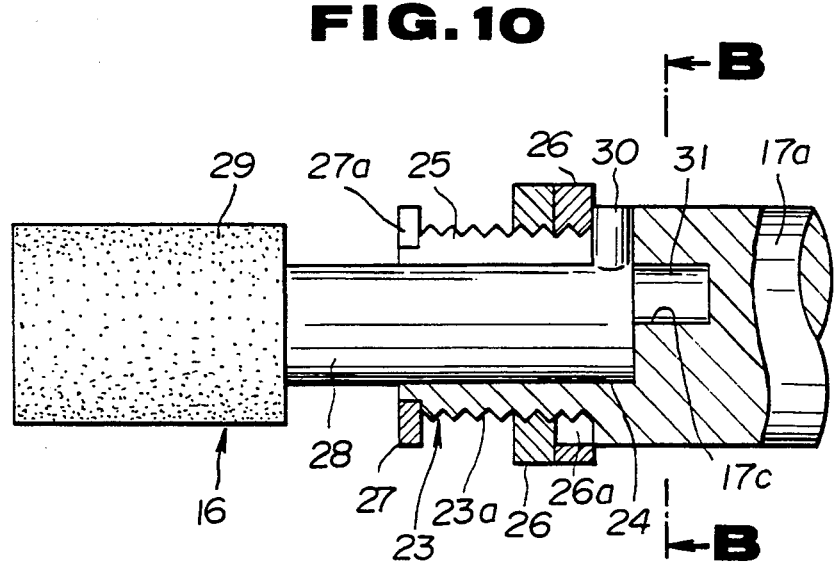
FIGS. 10 and 11 relate to the second embodiment of the present invention.
Figure 11:
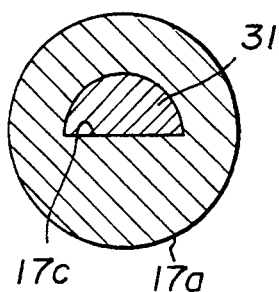

Next, the second embodiment of the invention is explained in conjunction with FIGS. 10 and 11. In this embodiment, a projection 31 having a semicircular cross section is formed at the back of a support axis 28 of a rotating treatment member 17, and a receiving hole 17c into which the projection 31 is fitted is created on the bottom of a hollow 24 of a mount 23 for a first torque transmission member 17a. Torque is transmitted from the torque transmission member 17a to the rotating treatment member 16 via a slit 25, a protrusion 30, and the receiving hole 17c and projection 31. Compared with torque transmission by means of the engagement of the protrusion 30 and slit 25 according to the first embodiment, a motor capable of yielding larger torque can be employed. The other configuration is identical to that of the first embodiment.

Figure 12:
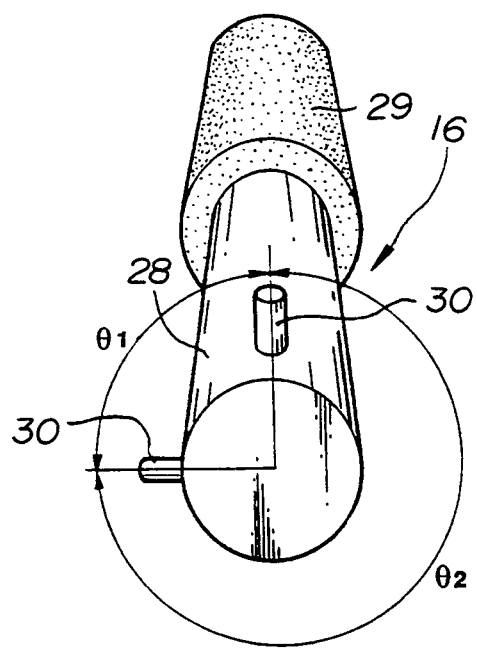
FIGS. 12 and 13 relate to the third embodiment of the present invention.
Figure 13:
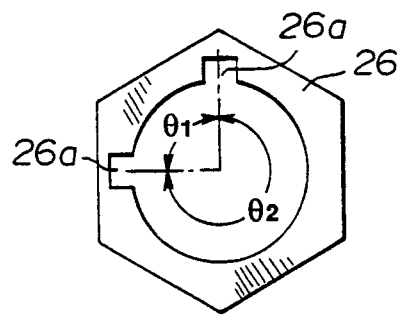

Next, the third embodiment is explained in conjunction with FIGS. 12 and 13. In this embodiment, two protrusions 30 are formed on the external circumference of a support axis 28 of a rotating treatment member 16, so that they cannot have a symmetry axis ($\theta 1 \neq \theta 2$). The clearance grooves 26a of a locking member and the slits 25 of a torque transmission member 17a (See FIG. 1) are formed at positions corresponding to the protrusions 30. The two slits 25 and protrusions 30 are engaged mutually to transmit torque to the rotating treatment member 16. Therefore, a motor providing larger torque can be employed. Since the protrusions 30 are located asymmetrically, the grooves 26a of the locking member 26 match the protrusions 30 once a rotation cycle. Therefore, even if the number of protrusions 30 increases, the possibility that the rotating treatment member 16 falls off because of loosened locking members is as extremely low as that of the first embodiment.

Based on the foregoing concept, the number of protrusions 30 positioned at nonuniform angles ($\theta 3 \neq \theta 4 \neq \theta 5$) and that of clearance grooves 26a of a locking member 26 corresponding to the protrusions 30 may be three, or four or more.

Figure 14:
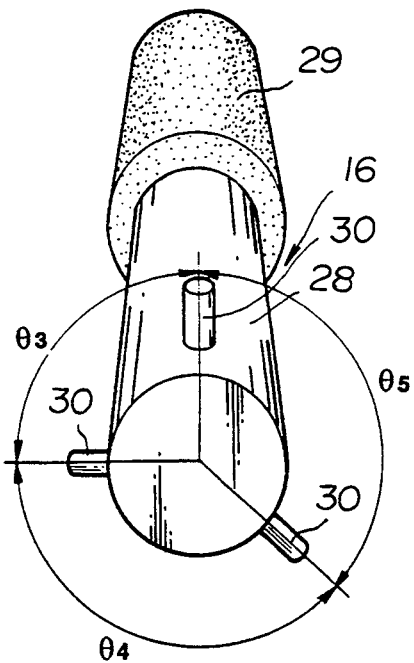
FIGS. 14 and 15 relate to a modified endoscope system of the third embodiment.
Figure 15:
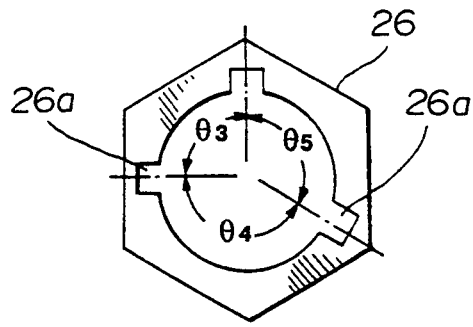

When the numbers of the protrusions 30 and clearance grooves 26a are three or more, if at least one of the interior angles of the protrusions 30 or clearance grooves 26a differs from the others, the protrusions 30 and clearance grooves 26a match mutually at only one point of a rotation cycle. Therefore, the interior angles in FIG. 14 may be set in such a way that $\theta 3 \neq \theta 4$, $\theta 3 \neq \theta 5$, and $\theta 4 \neq \theta 5$.

Next, the fourth embodiment is explained. In this embodiment, a rotating treatment member 16 can be replaced easily without using a tool.

Figure 16:
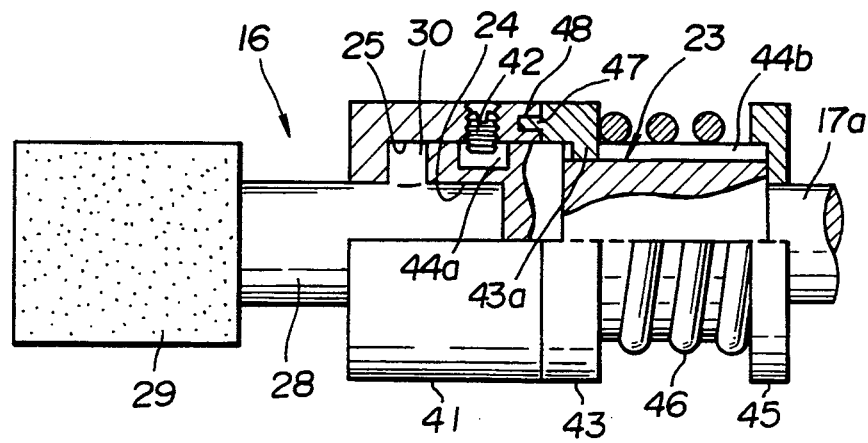
FIGS. 16 and 17 relate to the fourth embodiment of the present invention.

As shown in FIG. 16, the support axis 28 of a rotating treatment member 16 is fitted into a hollow 24 formed in the mount 23 of a torque transmission member 17a projecting from the distal end 12 of an endoscope 1 (See FIG. 1), and a protrusion 30 on the external circumference of the support axis 28 is fitted into a slit 25 formed on the edge of the mount 23.

Figure 17:
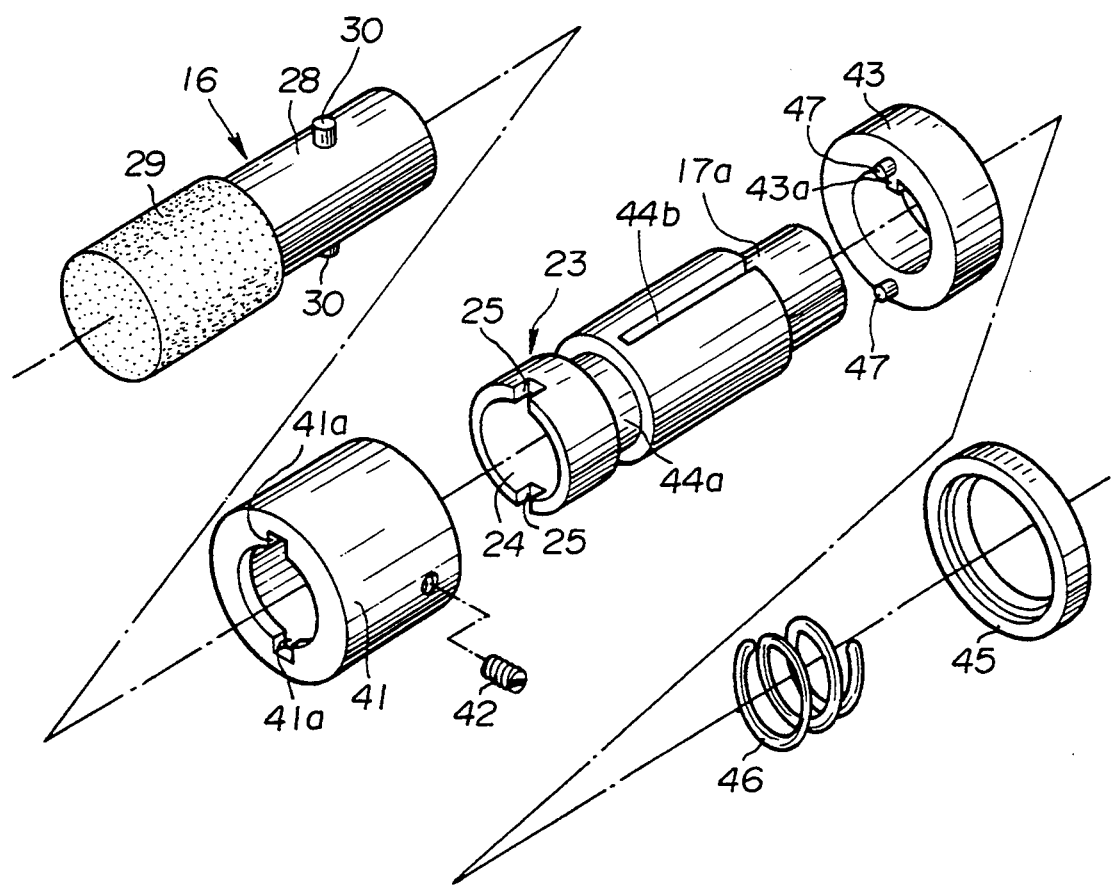

The mount 23 of the torque transmission member 17a is provided with a locking member 41 in such a way that the mount 23 will be shielded by the locking member 41. A clearance groove 41a (See FIG. 17) is formed at a position of the locking member 41 to be consistent with the slit 25. The end of a screw 42 inserted from the circumference of the locking member 41 is fitted into the groove 44a on the external circumference of the mount 23.

The axial movement of the locking member 41 is restricted by the screw 42 fitted into the groove 44a. When the locking member 41 is rotated to make the clearance groove 41a and slit 25 out of phase, the protrusion 30 of the rotating treatment member 16 can be locked in the slit 25.

A lock ring 43 is attached to the back surface of the locking member 41 of the mount 23. A key 43a projecting from the internal-diameter side of the lock ring 43 is fitted into a key groove 44b formed on the mount 23 and allowed to move only in the axial direction.

The back surface of the lock ring 43 is pressed toward the tip of the endoscope by a spring 46 stopping at a spring stopper 45 one end of which is fixed to the proximal side of the mount 23. The front surface of the lock ring 43 is pressed onto the back surface of the locking member 41. Positioning pins 47 are provided symmetrically on the front surface of the lock ring 43. Positioning holes 48 to which the positioning pins 47 are fitted are drilled on the back surface of the locking member 41.

As shown in FIG. 16, the positioning pins 47 and positioning holes 48 are secured at a position at which the clearance grooves 41a of the locking member 41 will be 90° out of phase with slits 25 formed on the mount 23.

To replace the rotating treatment member 16 mounted properly to the mount 23 of the torque transmission member 17a, the lock ring 43 must be, first, slided toward the proximal side of the mount 23 by withstanding the pressure of the spring 46. Then, the positioning pins 47 projecting from the front surface of the lock ring 43 are disengaged from the positioning holes 48 on the back surface of the locking member 41. Thus, the locking member 41 becomes rotatable freely.

Then, the locking member 41 is rotated so that the clearance grooves 41a formed on the locking member 41 will coincide with the slits 25 formed on the mount 23. Then, the rotating treatment member 16 is extracted so that a new rotating treatment member 16 can be mounted.

Then, the locking member 41 is rotated to fit the positioning pins 47 into the positioning holes 48. Thus, the rotating treatment member 16 is fixed to the torque transmission member 17a.

According to the foregoing embodiment, the rotating treatment member 16 can be replaced by a simple operation. This improves workability. Since the lock ring 43 is always pressed to the locking member 41 with the pressure of the spring 46, the engagement of the positioning pins 47 and positioning holes 48 will not be released by the influence of vibration.

Torque is transmitted to the rotating treatment member 16 without passing through the lock ring 43 and locking member 41. Therefore, no backlash occurs between the lock ring 43 and locking member 41 during rotation drive.

Figure 18:
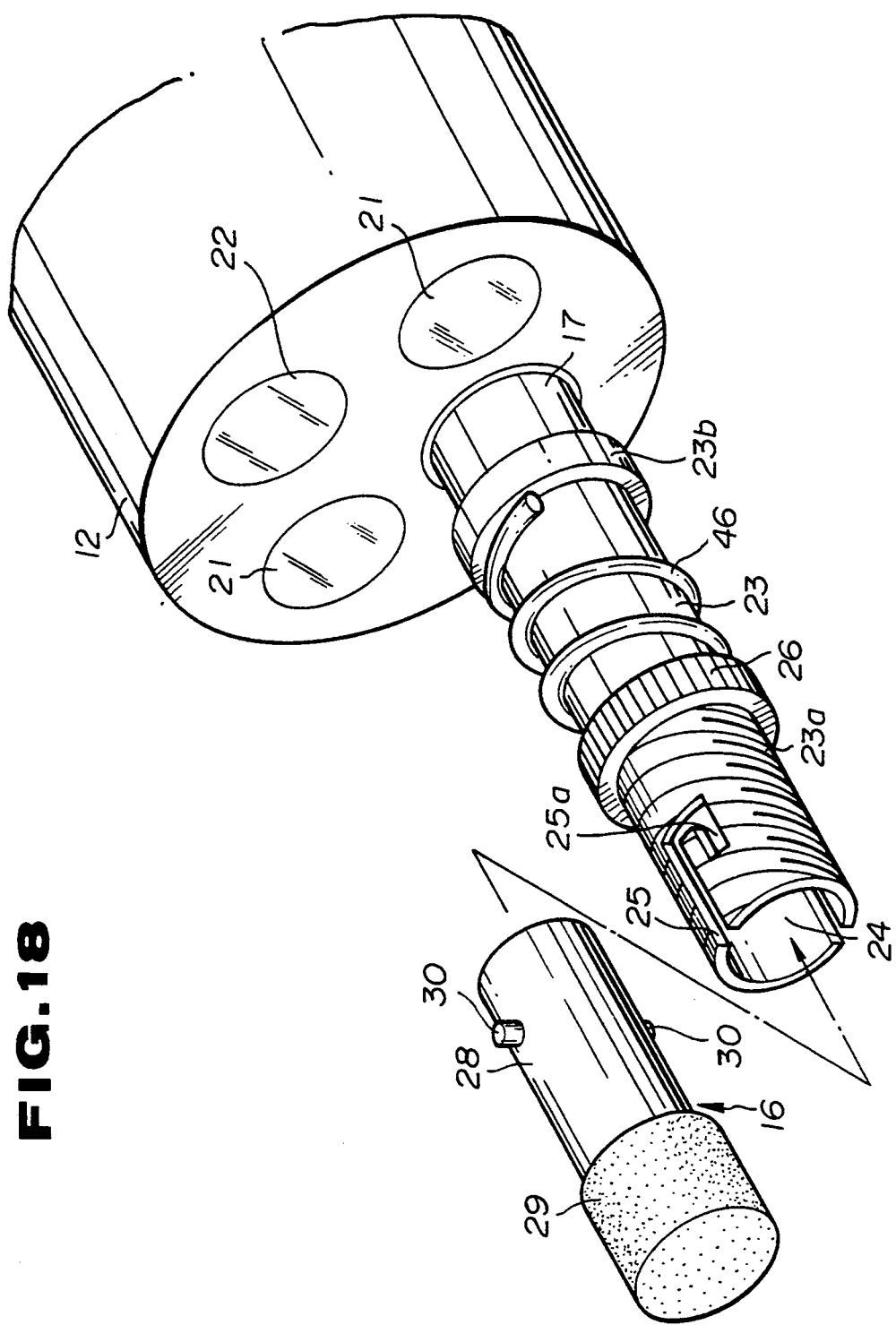
FIGS. 18 and 19 relate to the fifth embodiment of the present invention.
Figure 19:
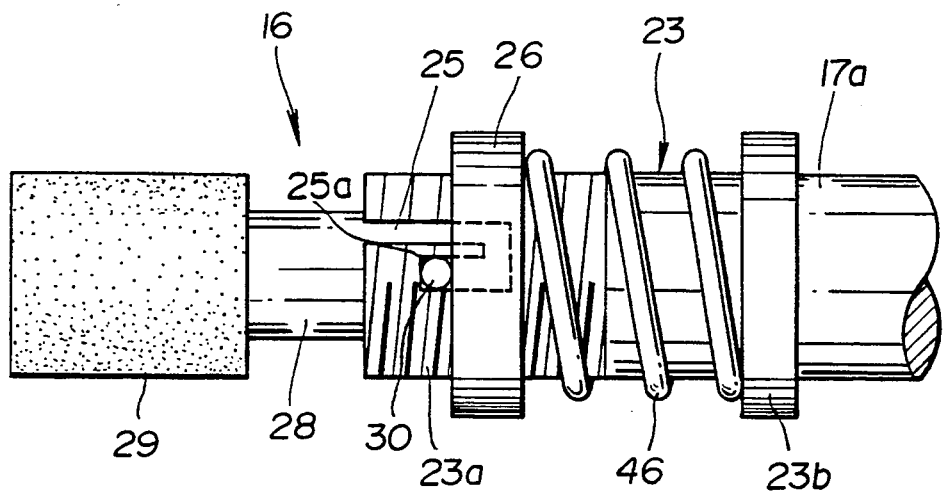

Next, the fifth embodiment is explained in conjunction with FIGS. 18 and 19. In this embodiment, a rotating treatment member 16 can be detached easily without using a tool.

As shown in FIG. 19, when a rotating treatment member 16 is properly mounted to a mount 23 of a torque transmission member 17, a protrusion 30 created on a support axis 28 of the rotating treatment member 16 is fitted into a J-shaped slit 25 formed on the mount 23, and a locking member 26 applied to a screw thread 23a created on the mount 23 is stopped by a stopper 25a oriented toward the tip of the slit 25.

The back surface of the locking member 26 is pressed toward the tip of the endoscope by a spring 46 one end of which stops at a flange 23b formed in the proximal portion of the mount 23.

To replace the rotating treatment member 16, the locking member 26 must be, first, rotated in the proximal direction by withstanding the pressure of the spring 46. Thus, the locking member 26 is moved to a position at which it is distanced from the slit 25 formed on the mount 23 (See FIG. 18).

Next, the protrusion 30 on the rotating treatment member 16 which is fitted into the slit 25 is moved along the slit 25 to extract a support axis 28 having the protrusion 30 from a hollow 24.

Then, the support axis 28 of a new rotating treatment member 16 is inserted into the hollow 24, so that the protrusion 30 on the support axis 28 will be fitted into the slit 25. Then the locking member 26 is used to lock the protrusion 30 in the stoppage section 25a of the slit 25.

In this embodiment, the locking member 26 receives the pressure of the spring 46 to press the protrusion 30 to the stoppage section 25a all the time. Therefore, the locking member 26 will not be loosened by the influence of vibration. If the locking member 26 should be loosened, it is re-tightened by the pressure of the spring 46. The area in which the locking member 26 may loosen is limited. As far as the locking member 26 is positioned at the bending section of the slit 25, the rotating treatment member 16 will not come off from the mount 23.

Figure 20:
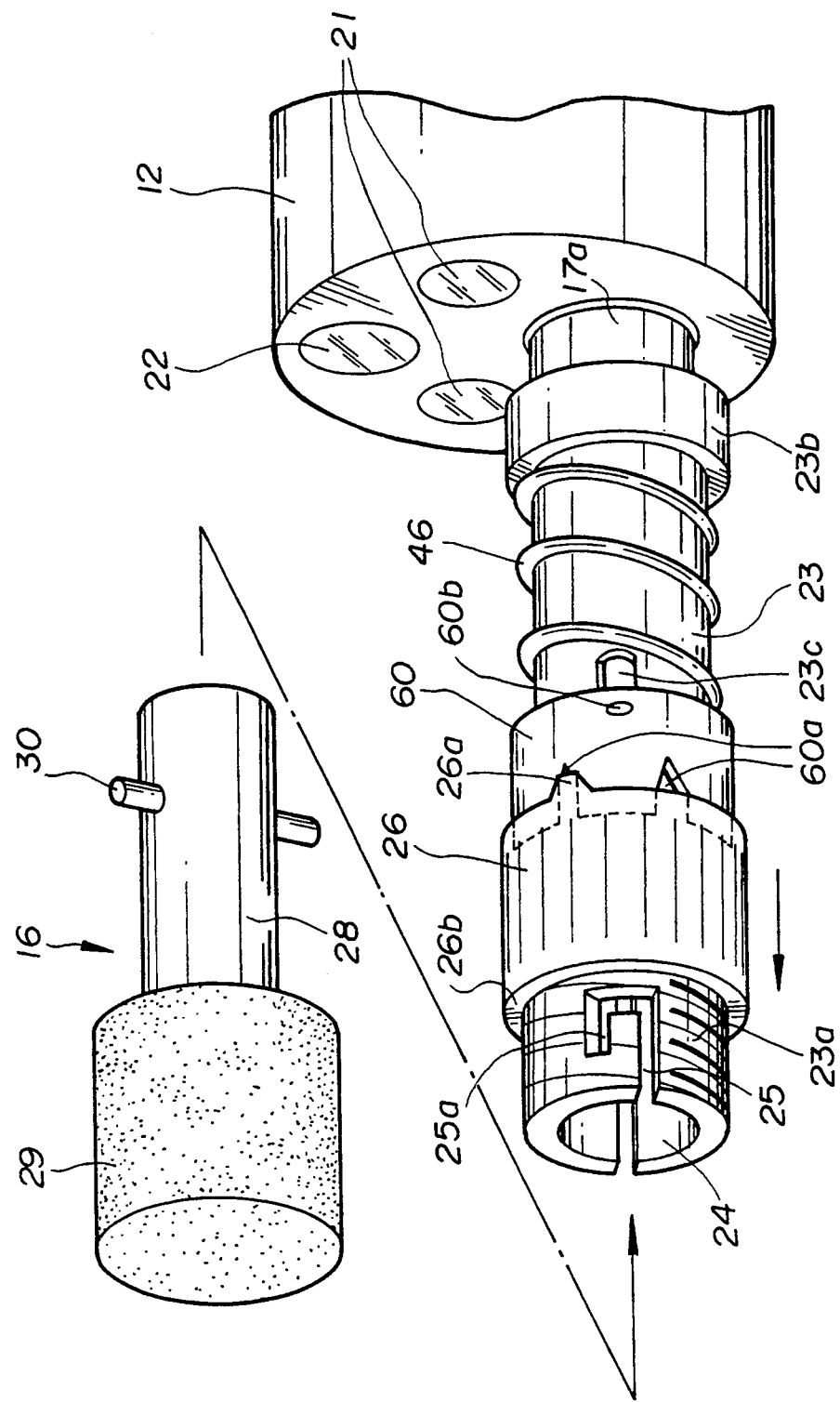
FIG. 20 is a perspective view showing the distal end of an endoscope according to the sixth embodiment of the present invention.

FIG. 20 is a perspective drawing of the distal end of an endoscope, showing the sixth embodiment of the present invention.

In this embodiment, a rotating treatment member 16 can be detached easily without using a tool.

As shown in FIG. 20, an almost J-shaped slit 25 is formed on the mount 23 of a torque transmission member 17a so that a protrusion 30 created on a support axis 28 can be stored in and slided along the J-shaped silt 25. A ring type locking member 26 is provided, on the internal circumference of which a screw is created to be engaged with a screw thread 23a created on the mount 23. Using the locking member 26, the protrusion 30 can be stopped at the deepest stoppage section 25a of the J-shaped slit 25.

The mount 23 is provided with a ring type rotation stoppage member 60 which can slide freely in the axial direction. To the rotation stoppage member 60, a pin 60b projecting inward in the radial direction is adhered, for example, with adhesive. The pin 60b is located in a groove 23c elongated in the axial direction of the mount 23. A plurality of concave portions 60a extending in the axial direction is formed on the edge of the rotation stoppage member 60, then a convex portion 26a which is formed at the proximal end of the locking member 26 and projecting inward in the radial direction is engaged with one of the concave portions 60a.

The back of the ring type rotation stoppage member 60 which is freely movable is pressed toward the tip of the endoscope by a coil spring or other elastic member 46 one end of which is stopped by a large-diameter flange 23b formed at the proximal part of the mount 23. Therefore, the locking member 26 is also pressed toward the tip of the endoscope via the rotation stoppage member 60.

To mount and fix the rotation treatment member 16, the support axis of the rotation treatment member 16 must be inserted into the hollow 24, first. Then, the protrusion 30 projecting from the support axis 28 is fitted into the slit 25, then the locking member 26 is used to lock the protrusion 30 in the stoppage section 25a of the slit 25. Next, a grindstone is picked up with fingers, then the rocking member 26 is turned. Then, the convex portion 26a goes beyond the concave portions 60a of the rotation stoppage member 60. The locking member 26 moves in the axial direction along the screw thread 23a. At this time, part of the pin 60b is positioned in the groove 23c. Therefore, the rotation stoppage member 60 does not rotate. The locking member 26 is rotated and moved toward the rotating treatment member 16. When the front surface 26b of the locking member 26 touches the protrusion 30 of the rotating treatment member 16 located in the stoppage section 25a, the locking member 26 is turned slightly so that the convex portion 26a will be engaged with a nearest concave portion 60a. Thus, the rotation treatment member 16 is locked.

In the sixth embodiment, even when the rotating treatment member 16 is rotated clockwise or counterclockwise, torque generated in the support axis 28 during grinding is received by the slit 25. Therefore, the rotating treatment member 16 will not fall off. The locking member 26 will not be loosened by vibration, because the convex portion 26a is engaged with a concave portion 60a of the rotation stoppage member 60.

The seventh embodiment of the present invention is explained in conjunction with FIG. 21 below.

In this embodiment, a rotating treatment member 16 can be detached easily without using a tool.

As shown in FIG. 21, an elastic bar 26c is fixed in parallel with the axis in the proximal side of a locking member 26. A plurality of stoppers 60c extending outward in the radial direction is formed in a rotation stoppage member 60.

The other configuration is identical to that of the sixth embodiment.

In the seventh embodiment having the aforesaid configuration, when the locking member 26 is turned, the elastic bar 26c confronts with the stopper 60c. When the locking member 26 is rotated further, the elastic bar 26c deforms to go beyond the stopper 60c. Then, the locking member 26 moves in the axial direction along a screw thread 23a.

The other functions and effects are identical to those of the sixth embodiment.

Figure 22:
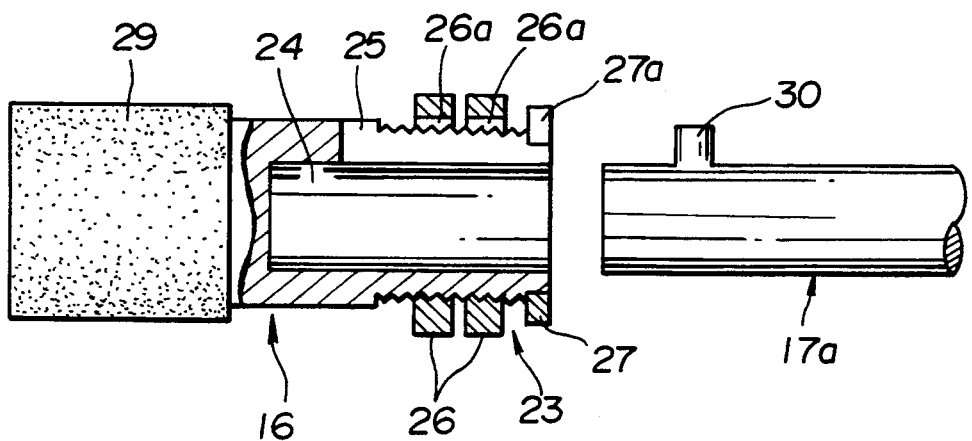
FIG. 22 is a side view showing a torque transmission member and a rotating treatment member according to the eighth embodiment of the present invention.

In the foregoing embodiment, the tip (distal end) of a torque transmission member 17a is provided with a hollow 24 for storing the proximal portion of a support axis 28 of a rotating treatment member 16, and a slit 25 for guiding and storing a protrusion 30 on the proximal portion. However, the present invention is not confined to this configuration. A mount 23 may be formed to have the hollow 24 and slit 25 in the proximal portion of the support axis of the rotation treatment member 16. Then, the protrusion 30 to be fitted into the slit 25 may be created in the distal portion of the torque transmission member 17a. For example, when this concept applies to the first embodiment shown in FIG. 2, the configuration of the eighth embodiment shown in FIG. 22 will be realized.

This concept can apply to other embodiments (second to seventh embodiments).

The ninth embodiment of the present invention is explained below.

Figure 23:
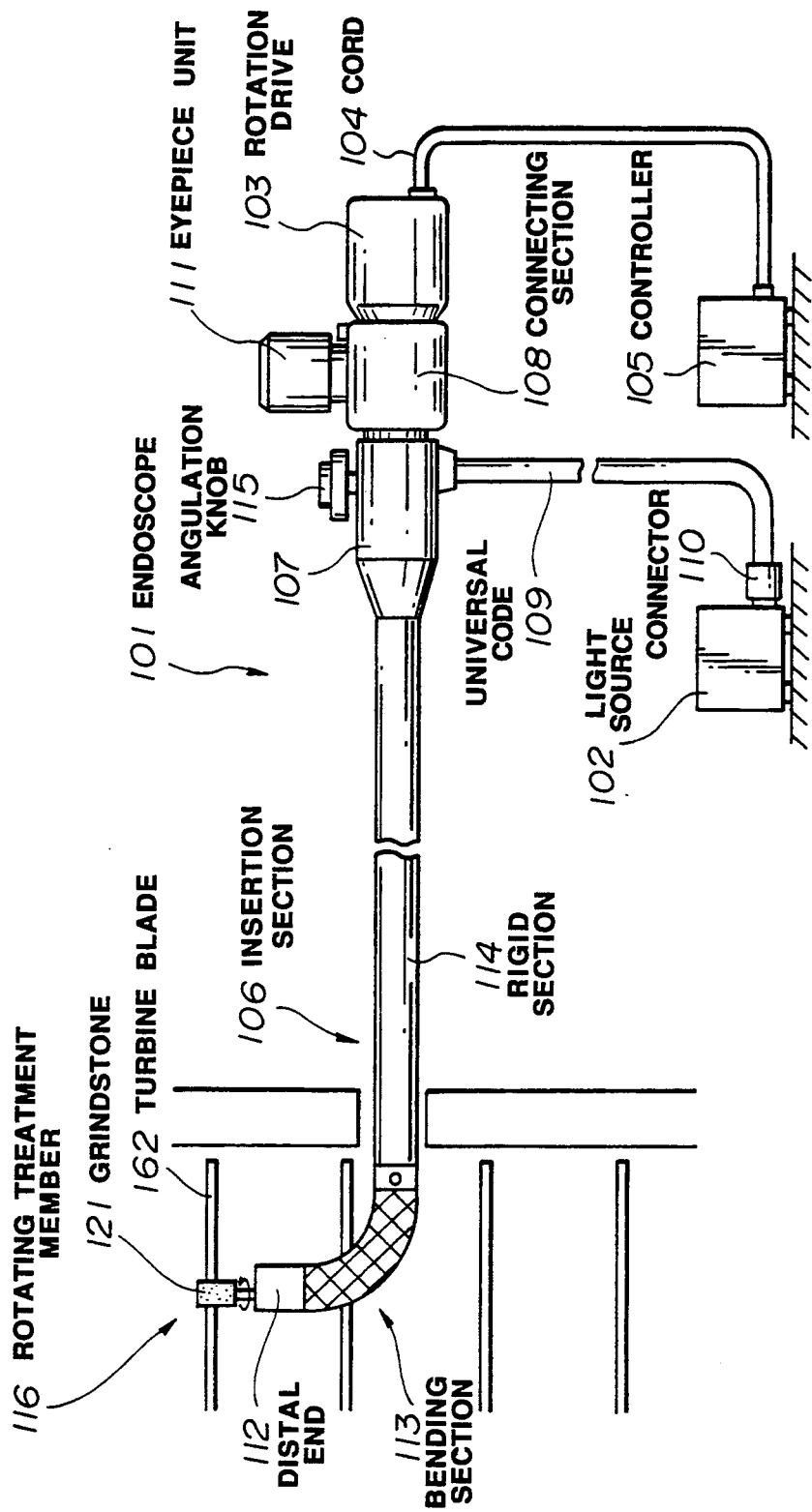
FIGS. 23 to 28 relate to the ninth embodiment.

As shown in FIG. 23, an endoscope system according to the present invention comprises an endoscope 101 having an observation optical system and an illumination optical system, a light source 102 which is connected to the endoscope and supplies illumination light, a rotation drive 103 incorporating a rotation drive means, and a controller 105 which is connected to the rotation drive 103 via a cord 104.

The endoscope 101 comprises an elongated insertion tube 106, a control section 107 coupled to the back of the insertion tube 106, a connecting section 108 coupled to the back of the control section 107, and a universal cord 109 extending laterally from the control section 107. The end of the universal cord 109 is provided with a connector 110 which is connected to the light source 102 so that it can be detached freely. An eyepiece unit 111 incorporating an eyepiece optical system for observing things with naked eyes is installed in the side of the connecting section 108.

The insertion tube 106 is divided into a rigid distal end 112, a bending section 113 which can bend, and a rigid section 114 in that order from the tip of the endoscope.

An angulation knob 115 for bending the bending section 113 is installed on the side of the control section 107.

Figure 24:
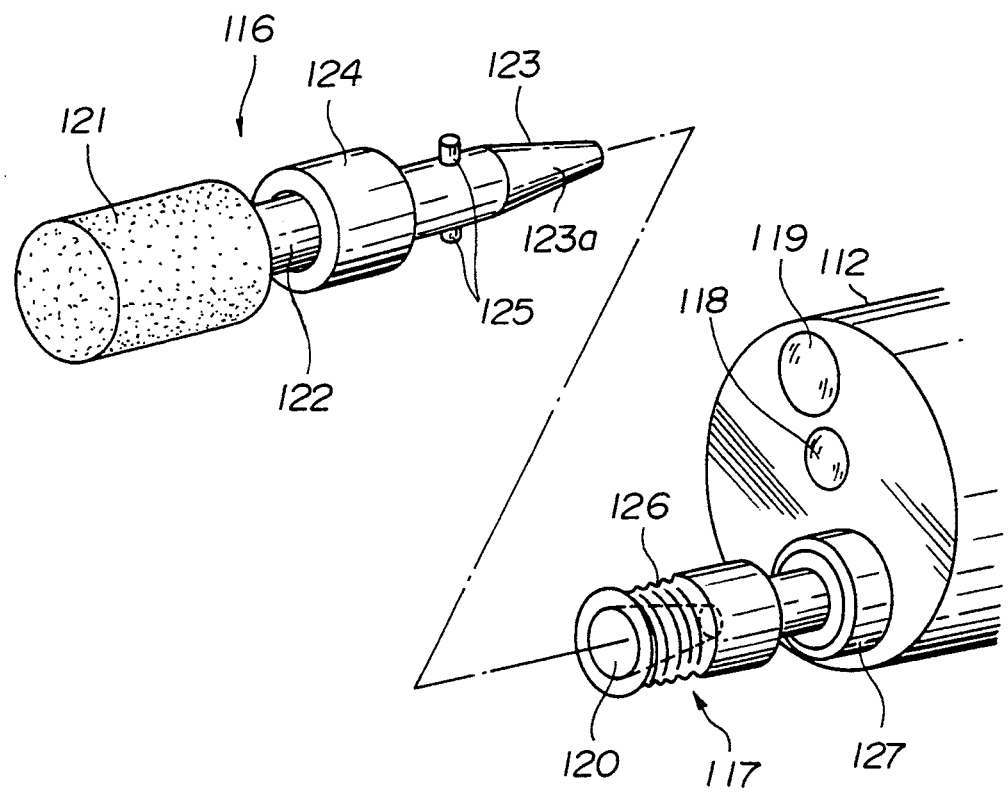

The end surface of the distal end 112 is provided, for example, with a torque transmission section 117 from which a rotating treatment member 116 is detached, an illumination optical system 118 for emitting illumination light, and an objective optical system 119 for observing objects as shown in FIG. 24.

The back of the rotating treatment member 116 or the proximal end of an axis 122 forms a conical section 123 having a conical tapered surface 123a. The conical section 123 is engaged with a conical hollow 120 in the torque transmission section 117. The apex of the conical section 123 is cut off and flattened. A means for grinding or abrading touching parts; such as, a grindstone 121 is attached to the tip of the axis 122. The portion of the axis 122 between the conical section 123 and grindstone 121 is provided with a locking ring 124 having a female screw. Moreover, a pin 125 for preventing the locking ring 124 from coming off in the axial direction is penetrating the axis 122.

The female screw of the fixing ring 124 is engaged with a male screw 126 formed on the external circumference of the conical hollow 120 in the torque transmission section 117, thus pressing the pin 125 in the A direction. The torque transmission section 117 is supported by a rotation support member 127 mounted to the distal end 112 of the endoscope to be freely rotatable. The conical section 123 of the rotating treatment member 116 is engaged with the conical hollow 120 of the torque transmission section 117, wherein the angle of the tapered surface 123a of the conical section 123 is set to a given value or a smaller value.

Figure 25:
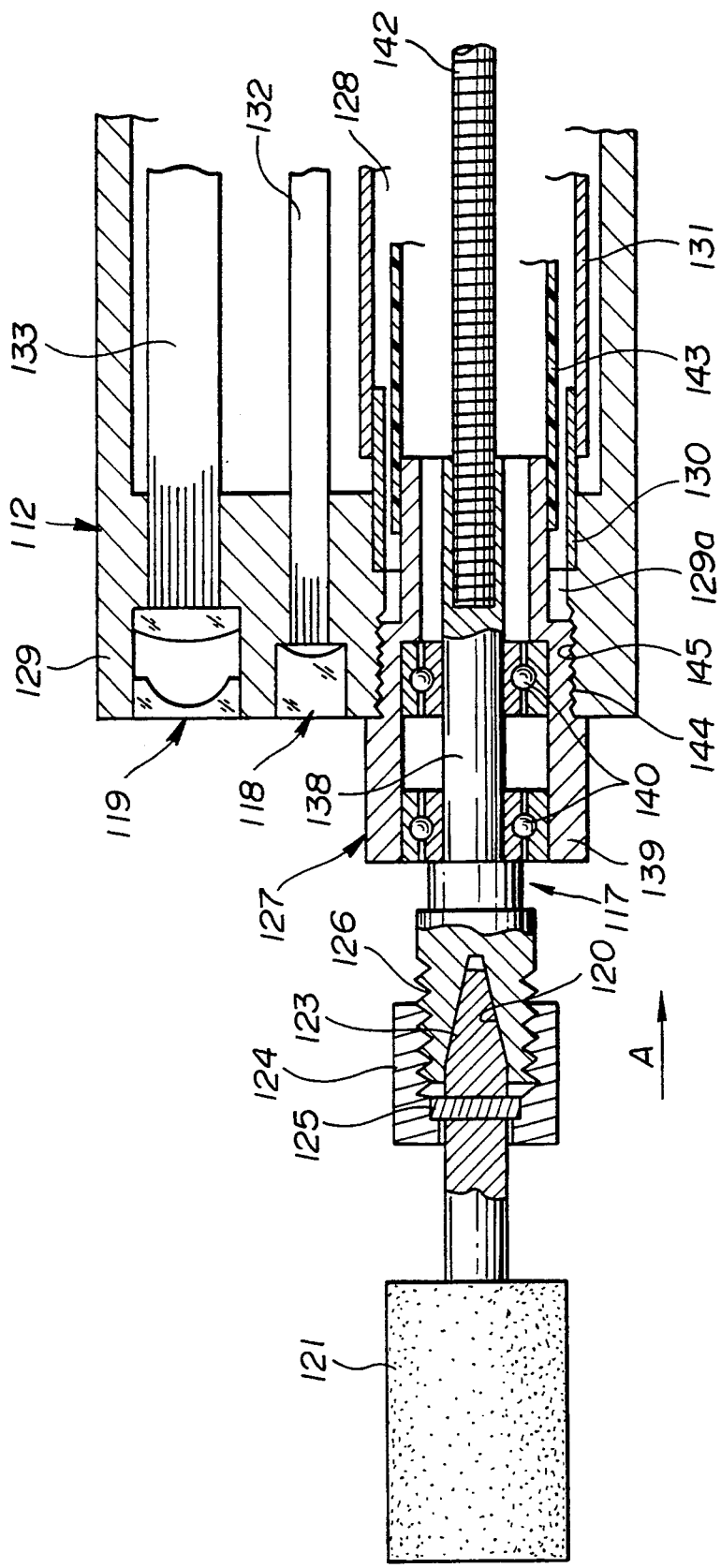
Figure 27:
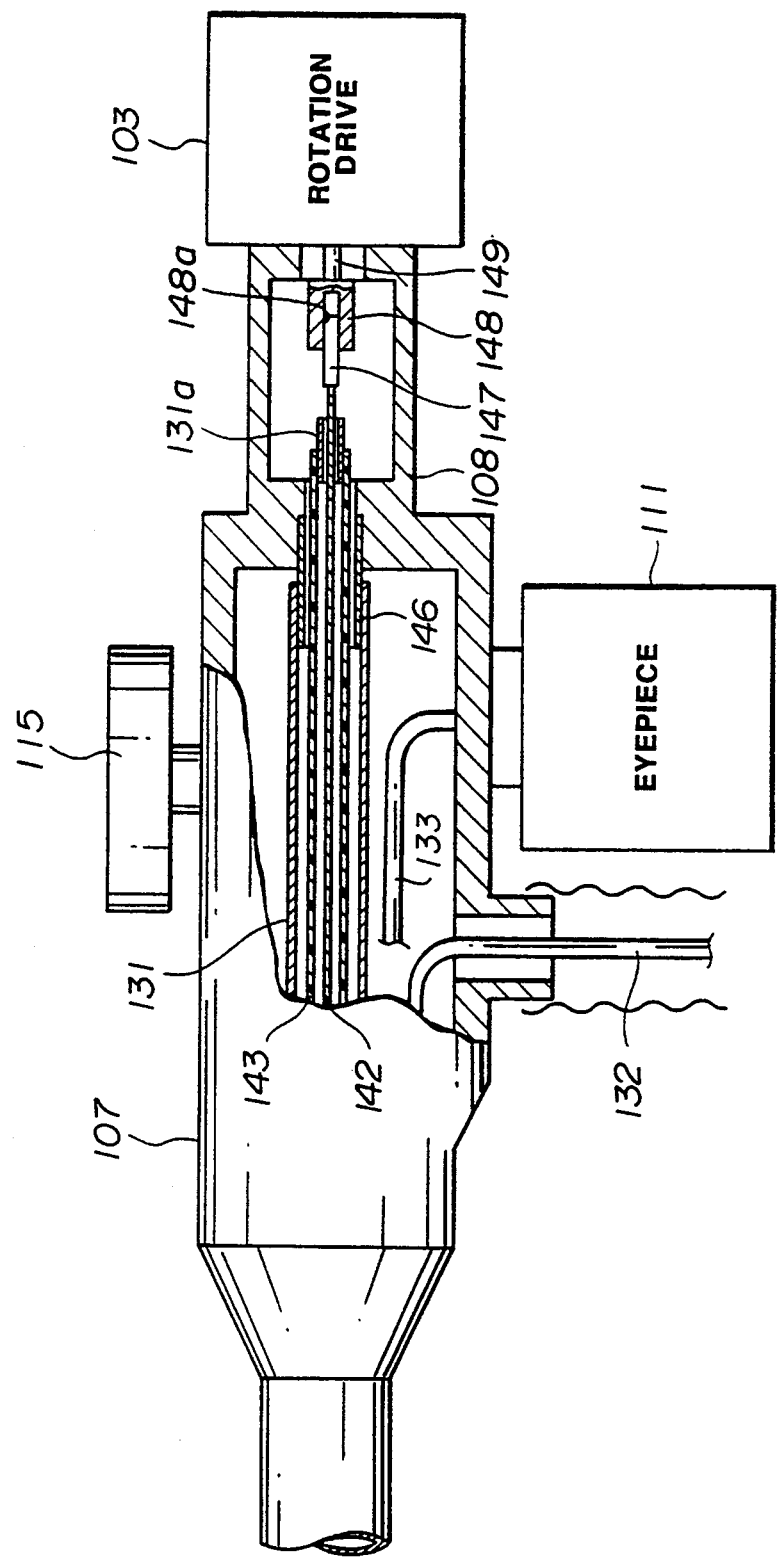

As shown in FIG. 25, a channel 128 is formed in the distal end 112. The channel 128 comprises a hollow 129a of a rigid main unit (distal end) 129, a base 130 fixed to the hollow 129a, and a flexible tube 131. The tube 131 passes through the bending section 113, rigid section 114, and control section 107, then opens in the connecting section 108 via the base 131a as shown in FIG. 27. Light guide fibers 132 for propagating illumination light are running through the illumination optical system 118. The back of the light guide fibers 132 is routed to the connector 110 attached to the light source 102, thus propagating illumination light supplied from the light source 102 and emitting it forward through the illumination optical system 118.

On the other hand, image guide fibers 133 for transmitting formed optical images are running through the objective optical system 119. One (distal) end surface of the image guide fibers 133 is arranged at the focal point of the objective optical system 119, while the back is bent to reach the eyepiece unit 111.

Figure 26:
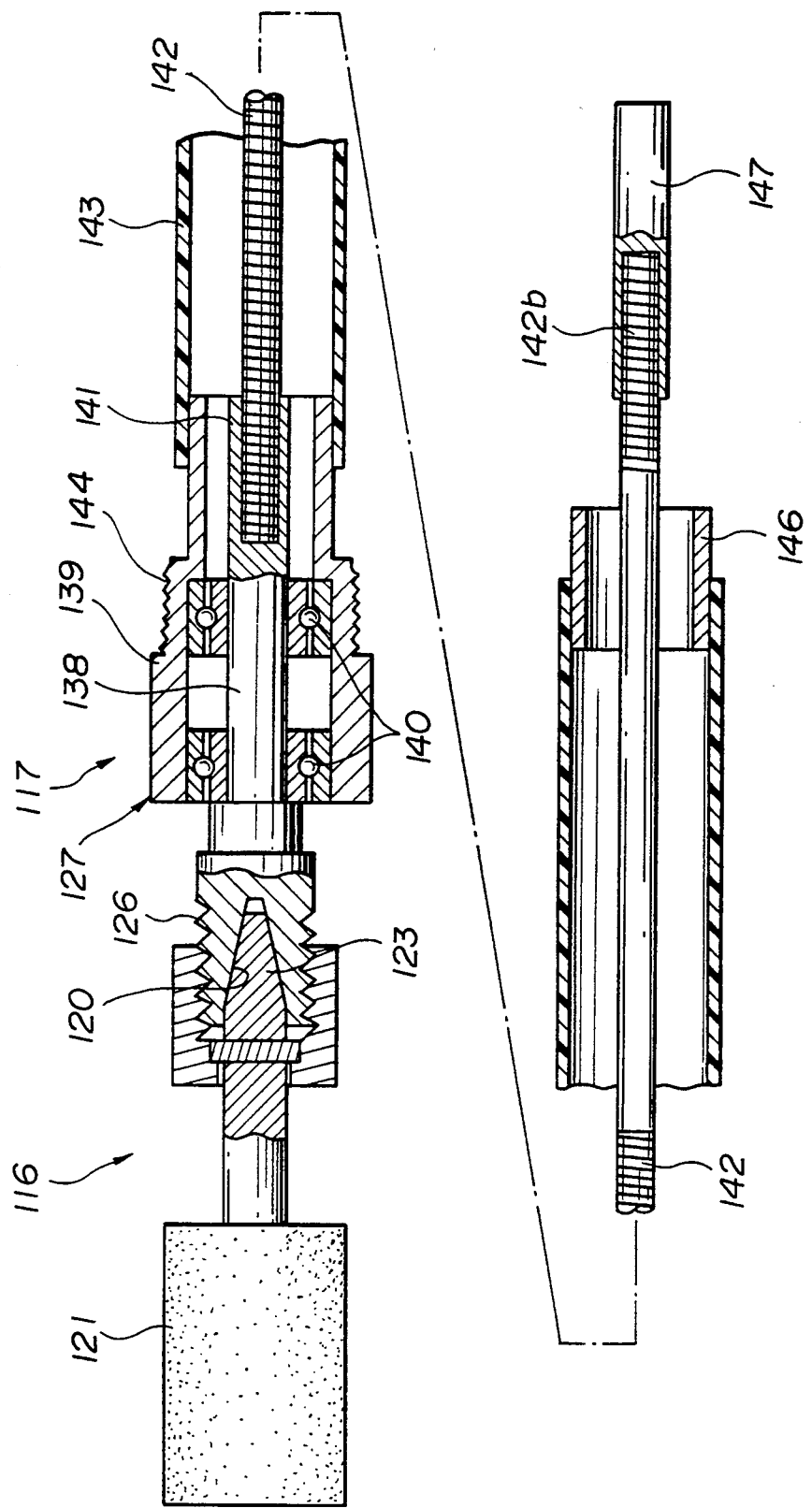

FIG. 26 shows the rotating treatment member 116 and torque transmission section 117.

A shaft 138 with the conical hollow 120 at the end is supported by ball bearings 140 housed in a casing 139 forming a rotation support member 127 to be freely rotatable. A flexible shaft 142 is stuck to a recess in the back 141 of the shaft 138 by, for example, brazing. The external circumference of the flexible shaft 142 is provided with a protective tube 143. Then, as shown in FIG. 25, the torque transmission section 117 is inserted into the channel 128, and the male screw 144 of the casing 139 is engaged with the female screw 145 of the main unit 129.

Figure 28:
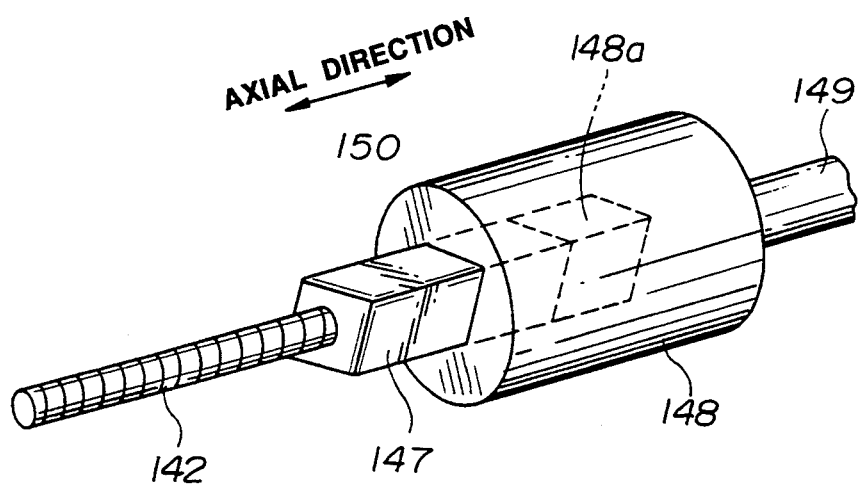

The back 142b of the flexible shaft 142 is connected to a first joint 147 projecting from the base 146 stuck to the back of the tube 143. The first joint 147 is, as shown in FIG. 26, attached to the shaft 149 of the rotation drive 103 via a second joint 148. These two joints 147 and 148 are shown in FIG. 28.

The first joint 147 fixed to the back of the flexible shaft 142 is, for example, a cube, which is designed to be fitted into a space 148a of the second joint 148. Thus, the first joint 147 having a cubic shape and the second joint 148 having a concave portion to be engaged with the cube are used to transmit torque. Moreover, the space 148a is elongated in the axial direction 150 so that an error in the length of the flexible shaft 142 can be absorbed by moving the first joint 147 in the axial direction 150.

In this embodiment, the torque transmission section 117 and flexible shaft 142 can be disconnected from the channel 128. This helps insert a foreign matter collector to collect foreign matters.

The functions of the foregoing embodiment are explained below.

The rotation drive 103 drives the flexible shaft 142 and torque transmission section 117. The rotating treatment section 116 fitted into the conical hollow 120 of the torque transmission section 117 is provided with torque by the friction force of the tapered surface 123a. Thus, the grindstone 121 is driven to grind, for example, the edge of a turbine blade 162 shown in FIG. 23.

According to the ninth embodiment, torque is transmitted from the torque transmission section 117 to the rotating treatment member 116 using the friction force of the tapered surface 123a.

The rotating treatment member is not limited to a grindstone. A cutting blade may be employed.

By combining parts of the aforesaid embodiments, different embodiments can be constituted.

What is claimed is:

1. An endoscope system comprising:

an elongated insertion tube;

an illumination light emitting means which is installed in the tip of said insertion tube and emits illumination light;

an objective optical system which is installed in the tip of said insertion tube and forms optical images;

a torque transmission member which is installed at least in the tip of said insertion tube and outputs received torque from a mount installed at its distal end, said mount having a slit;

a rotating treatment member which is mounted to said mount to be freely detachable, and includes an axis and a protrusion on the external circumference near the proximal end thereof and a rotating treatment section which is formed as part of the distal end of said axis and grinds a touching object when it is driven to rotate, wherein said protrusion is fitted into said slit for removably mounting said rotating treatment member, along said axis thereof, into said mount; and a locking member having an axial end, wherein said axial end directly abuts said protrusion for locking said protrusion fitted in said slit.

2. An endoscope system according to claim 1, wherein said objective optical system includes a focal surface in which one end of an image guide having a function for transferring optical images is arranged.

3. An endoscope system according to claim 1, wherein said insertion tube includes a bending section which can be bent freely.

4. An endoscope system according to claim 1, wherein said torque transmission member is driven by a motor to rotate.

5. An endoscope system according to claim 4, further comprising a foot switch for changing the rotating direction of said motor.

6. An endoscope system according to claim 1, wherein said rotating treatment member is a grindstone.

7. An endoscope system according to claim 1, wherein said mount comprises a male screw thread, formed in the axial direction, on the external circumference of a distal end of said mount, said slit passing through said distal end of said mount and said male screw thread, and wherein said mount further comprises a female screw having a groove for passing said protrusion.

8. An endoscope system according to claim 7, wherein said male screw thread can apply to a female screw other than said female screw.

9. An endoscope system according to claim 7, wherein a ring for preventing said female screw from falling off is fixed to the distal end of said male screw thread.

10. An endoscope system according to claim 1, wherein the proximal end surface of said axis is provided with a convex portion and said mount is provided with a concave portion into which said convex portion is fitted.

11. An endoscope system according to claim 1, wherein said protrusions are installed at a plurality of positions on the external circumference near the proximal end of said rotating treatment member.

12. An endoscope system according to claim 1, wherein a plurality of said protrusions are installed at a plurality of rotation-asymmetric positions on the external circumference near the proximal end of said rotating treatment member.

13. An endoscope system according to claim 1, wherein said mount includes said slit formed at the entry of said mount and includes, through the side of said mount, a notch which is engaged with the distal end of said mount for accommodating therein said protrusion, and a ring member having a screw to be fitted into a circumferential groove on said mount.

14. An endoscope system according to claim 13, further comprising a rotation limit means for preventing said ring member from rotating.

15. An endoscope system according to claim 14, wherein said rotation limit means includes a concave portion formed on the edge of said ring member and a second ring member having a convex portion to be fitted into said concave portion is on one edge matching the edge of said ring member and a convex portion to be fitted into a groove, in the axial direction, on said mount.

16. An endoscope system according to claim 15, further comprising a restriction means for restricting an axial movement of said second ring member.

17. An endoscope system according to claim 1, wherein said mount includes a male screw thread formed in the axial direction on the external circumference of the distal end of said mount, a hollow created in said axial direction in the distal end of said cylindrical axis, said slit being in a J-shaped form and passing through said hollow and said male screw thread, and a female screw which is engaged with said male screw thread and restricts said axial movement of said protrusion stored in an innermost portion of said slit.

18. An endoscope system according to claim 17, further comprising a restriction means for preventing said male screw thread and said female screw from disengaging mutually.

19. An endoscope system according to claim 18, wherein said restriction means is a spiral coil spring.

20. An endoscope system according to claim 17, further comprising a rotation limit means for preventing the rotation of said Female screw engaged with said male screw thread.

21. An endoscope system according to claim 20, wherein said rotation limit means includes projections, which are formed at a plurality of positions in the circumferential direction of said female screw, extending inward in the radial direction, a ring member in which notches, to which said projections are fitted, are formed on one edge, and a pin fitted into a groove extending in a direction along said axis.

22. An endoscope system according to claim 20, wherein said rotation limit means comprises an elastic bar projecting in the axial direction on the external circumference of said female screw, a ring member including convex portions, which are capable of stopping said bar, said convex portions formed at a plurality of positions on the external circumference of said female screw and a pin fitted into a groove extending in a direction along said axis.

23. An endoscope system according to claim 21 or 22, further comprising a restriction means for restricting said axial movement of said ring member.

24. An endoscope system comprising:
an elongated insertion tube;
an illumination light emitting means which is installed in the tip of said insertion tube and emits illumination light;
an objective optical system which is installed in the tip of said insertion tube and forms optical images;

a torque transmission member which is installed at least in the tip of said insertion tube and outputs transmitted torque from a terminal to a distal end thereof;

a rotating treatment member, having an axis, which is mounted to said distal end to be freely detachable and a rotating treatment section which is formed as part of the distal end along said axis of said rotating treatment member, wherein said rotating treatment section grinds a touching object when driven to rotate, wherein a protrusion near a proximal end of said rotating treatment member is fitted into a slit formed at said distal end; and a locking member having an axial end, wherein said axial end directly abuts said protrusion for locking said protrusion fitted into said slit.

25. An endoscope system comprising:

an elongated insertion tube;

an illumination light emitting means which is installed in the tip of said insertion tube and emits illumination light;

an objective optical system which is installed in the tip of said insertion tube and forms optical images;

a torque transmission member which is installed at least in the tip of said insertion tube and outputs transmitted torque from a terminal to a distal end thereof; and a rotating treatment member, having an axis, which is mounted to said distal end to be freely detachable and a rotating treatment section which is formed as part of the distal end along said axis of said rotating treatment member, wherein said rotating treatment section grinds a touching object when driven to rotate, said rotating treatment member being locked in said torque transmission member by a falling prevention means for locking a protrusion, near a proximal end of said rotating treatment member, within a slit formed at said distal end, and for directly abutting an axial end of a locking member onto said protrusion fitted in said slit.

* * * * *